(12) United States Patent
Liu et al.

(10) Patent No.: US 11,354,926 B2
(45) Date of Patent: Jun. 7, 2022

(54) ULTRASOUND FINGERPRINT DETECTION AND RELATED APPARATUS AND METHODS

(71) Applicant: BFLY Operations, Inc., Guilford, CT (US)

(72) Inventors: Jianwei Liu, Fremont, CA (US); Keith G. Fife, Palo Alto, CA (US); Sarp Satir, San Francisco, CA (US)

(73) Assignee: BFLY OPERATIONS, INC., Guilford, CT (US)

( * ) Notice: Subject to any disclaimer, the term of this patent is extended or adjusted under 35 U.S.C. 154(b) by 303 days.

(21) Appl. No.: 16/705,504

(22) Filed: Dec. 6, 2019

(65) Prior Publication Data

US 2020/0184177 A1 Jun. 11, 2020

Related U.S. Application Data

(60) Provisional application No. 62/776,992, filed on Dec. 7, 2018.

(51) Int. Cl.
*G06K 9/00* (2022.01)
*G06V 40/13* (2022.01)
(Continued)

(52) U.S. Cl.
CPC ........ *G06V 40/1306* (2022.01); *B06B 1/0276* (2013.01); *B06B 1/0292* (2013.01); *H01L 27/3234* (2013.01); *B06B 2201/70* (2013.01)

(58) Field of Classification Search
CPC .. G06K 9/0002; G06K 9/2018; B06B 1/0276; B06B 1/0292; B06B 2201/70;
(Continued)

(56) References Cited

U.S. PATENT DOCUMENTS 8,601,876 B2 12/2013 Schneider et al.
9,067,779 B1 6/2015 Rothberg et al.
(Continued)

FOREIGN PATENT DOCUMENTS

| CA | 2 976 829 A1 | 5/2017 |
| CN | 100378997 C | 4/2008 |
| WO | 2017/222964 A1 | 12/2017 |

OTHER PUBLICATIONS

International Search Report and Written Opinion dated Feb. 25, 2020 in connection with International Application No. PCT/US2019/064839.
(Continued)

*Primary Examiner* — Abdul-Samad A Adediran
(74) *Attorney, Agent, or Firm* — Osha Bergman Watanabe & Burton LLP

(57) ABSTRACT

Aspects of the technology described herein relate to sensing a fingerprint of a subject via an ultrasound fingerprint sensor. Certain aspects relate to transmitting and receiving ultrasound data at multiple different frequencies to provide sensing data from different depths within the skin of the subject. Since different ultrasound frequencies are expected to penetrate a subject's skin to different degrees, sensing a finger at multiple ultrasound frequencies may provide information on different physical aspects of the finger. For instance, sound ultrasound frequencies may sense a surface of the skin, whereas other ultrasound frequencies may penetrate through one or more of the epidermal, dermal or subcutaneous layers. The ultrasound fingerprint apparatus may have utility in various applications, including but not limited to mobile electronic devices, such as mobile phones or tablet computers, a laptop computer or biometric access equipment.

19 Claims, 11 Drawing Sheets

(51) Int. Cl.
*B06B 1/02* (2006.01)
*H01L 27/32* (2006.01)

(58) Field of Classification Search
CPC . H01L 27/3234; H01L 41/047; A61B 8/4483; A61B 8/14; G01N 29/2406; G06V 40/1306
USPC .............................................. 367/87; 600/440
See application file for complete search history.

(56) References Cited

U.S. PATENT DOCUMENTS

| | | | |
|---|---|---|---|
| 9,242,275 | B2 | 1/2016 | Rothberg et al. |
| 9,394,162 | B2 | 7/2016 | Rothberg et al. |
| 9,499,392 | B2 | 11/2016 | Rothberg et al. |
| 9,521,991 | B2 | 12/2016 | Rothberg et al. |
| 9,533,873 | B2 | 1/2017 | Rothberg et al. |
| 9,592,030 | B2 | 3/2017 | Rothberg et al. |
| 2007/0258628 | A1 | 11/2007 | Schneider et al. |
| 2008/0100572 | A1 | 5/2008 | Boillot |
| 2011/0055447 | A1 | 3/2011 | Costa |
| 2012/0206585 | A1 | 8/2012 | Schneider et al. |
| 2014/0313856 | A1* | 10/2014 | Taki ......................... A61B 8/14 367/87 |
| 2015/0032002 | A1* | 1/2015 | Rothberg ............. A61B 8/4483 600/440 |
| 2015/0036065 | A1 | 2/2015 | Yousefpor et al. |
| 2015/0165479 | A1 | 6/2015 | Lasiter et al. |
| 2016/0009544 | A1 | 1/2016 | Rothberg et al. |
| 2016/0019408 | A1 | 1/2016 | Liu et al. |
| 2016/0117541 | A1 | 4/2016 | Lu et al. |
| 2016/0163958 | A1 | 6/2016 | Park et al. |
| 2017/0110504 | A1 | 4/2017 | Panchawagh et al. |
| 2017/0320091 | A1 | 11/2017 | Budzelaar et al. |
| 2017/0320093 | A1* | 11/2017 | Chatterjee ............. H01L 41/047 |
| 2017/0323133 | A1 | 11/2017 | Tsai |
| 2017/0328866 | A1 | 11/2017 | Apte et al. |
| 2017/0330012 | A1 | 11/2017 | Salvia et al. |
| 2017/0360397 | A1 | 12/2017 | Rothberg et al. |
| 2017/0365774 | A1 | 12/2017 | Rothberg et al. |
| 2018/0029076 | A1* | 2/2018 | Van Rens .......... G01N 29/2406 |
| 2018/0101711 | A1 | 4/2018 | D'Souza et al. |
| 2018/0129849 | A1* | 5/2018 | Strohmann .......... G06K 9/2018 |
| 2018/0257927 | A1 | 9/2018 | Rothberg et al. |
| 2019/0197284 | A1* | 6/2019 | Park ..................... G06K 9/0002 |
| 2019/0231312 | A1 | 8/2019 | Fife et al. |
| 2019/0275561 | A1 | 9/2019 | Fife et al. |
| 2019/0336103 | A1 | 11/2019 | Fife et al. |
| 2019/0336104 | A1 | 11/2019 | Fife et al. |
| 2020/0013691 | A1 | 1/2020 | Liu et al. |
| 2020/0184176 | A1 | 6/2020 | Liu et al. |

OTHER PUBLICATIONS

International Search Report and Written Opinion dated Mar. 10, 2020 in connection with International Application No. PCT/US2019/064842.

[No Author Listed], Coating or Ceramics-covered Fingerprint Sensor. ZFS1650 Fingerprint Product Specification. ZEITEC Semiconductor. Aug. 2017, 23 pages.
[No Author Listed], Extending the leadership position in 2016. Fingerprint Cards Investor Update. Powerpoint Presentation. 39 pages, Dec. 9, 2015.
[No Author Listed], Fingerprint Individuality. Center for Unified Biometrics and Sensors. Powerpoint Presentation. 26 pages.
[No Author Listed], TrustOne Global. Powerpoint Presentation. 2013; 27 pages.
Bana et al., Fingerprint Recognition using Image Segmentation. (IJAEST) International Journal of Advanced Engineering Sciences and Technologies. 2011; 5(1):012-023.
Borukar et al., Fingerprint Security Using Image Processing. Sardar Patel Institute of Technology. 2012. 4 pages.
Boult et al., Biometrics—Practical Issues in Privacy and Security. University of Colarado at Colorado springs and Securics Inc. 2011; 53 pages.
Cherifi et al., Performance Evaluation of Behavioral Biometric Systems. Book on Behavioral Biometrics for Human Identification: Intelligent Applications. IGI. 2009; 22 pages.
Dolcourt, Galaxy S10 has an ultrasonic fingerprint scanner. Here's why you should care. clnet. Feb. 23, 2019. Retrieved from the Internet https://www.cnet.com/news/galaxy-s10-has-ultrasonic-fingerprint-scanner-heres-why-you-should-care-explainer (Last accessed Mar. 6, 2020).
Fons et al., Design of an Embedded Fingerprint Matcher System. IEEE Xplore. Conference Paper. Jan. 2006; 6 pages.
Fons et al., Embedded VLSI Accelerators for Fingerprint Signal Processing. IEEE. 2007; 6 pages.
Gok et al., Fingerprint Pre-processing on ARM and DSP Platforms. Elektronika IR Elektrotechnika. 2014: 20(6): 140-143.
Jin et al., Fingerprint Identification and Recognition Using Backpropagation Neural Network. 2002 Student Conference on Research and Development Proceedings. Shah Alam, Malaysia. IEEE. 2002; 98-101.
Lindeberg, How to Evaluate a Fingerprint Algorithm—and Achieve Top Performance. Precise Biometrics. Powerpoint Presentation. Jun. 25, 2015; 31 pages.
Maio et al., Direct Gray-Scale Minutiae Detection in Fingerprints. IEEE Transactions on Pattern Analysis and Machine Intelligence. Jan. 1997: 19(1): 27-40.
Thai et al., Fingerprint recognition using standardized fingerprint model. IJCSI International Journal of Computer Science Issues. May 2010: 7(3)(7): 11-17.
Tukur, Fingerprint Recognition and Matching using Matlab. The International Journal of Engineering and Science (IJES). 2015; 4(12):01-06.
Yuan et al., Fingerprint Liveness Detection Based on Multi-Scale LPQ and PCA. Image Detection and Analysis Technique. China Communications. Jul. 2016; 60-65.
International Preliminary Report on Patentability dated Jun. 17, 2021 in connection with International Application No. PCT/US2019/064842.
International Preliminary Report on Patentability dated Jun. 17, 2021 in connection with International Application No. PCT/US2019/064839.

\* cited by examiner

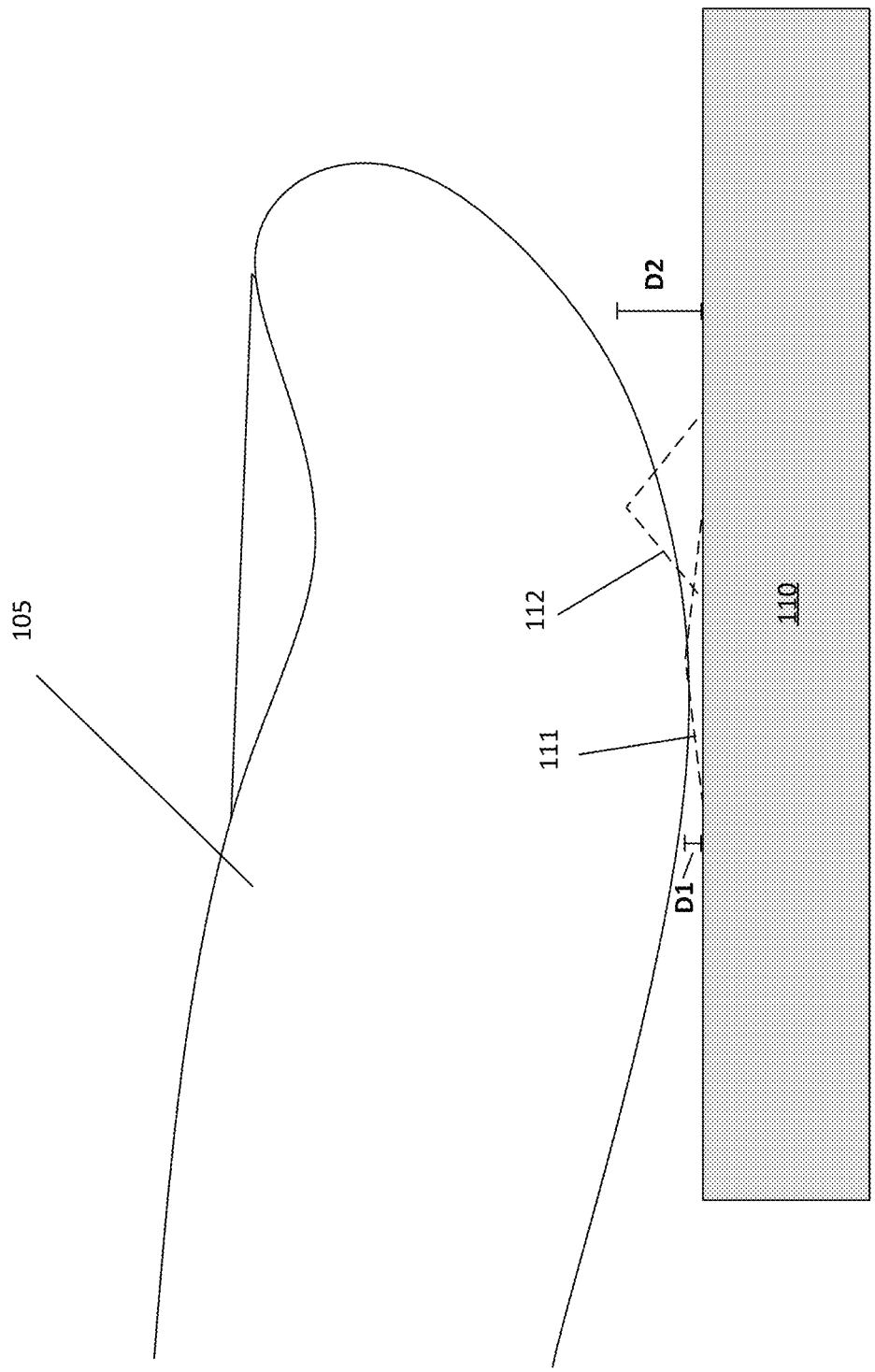

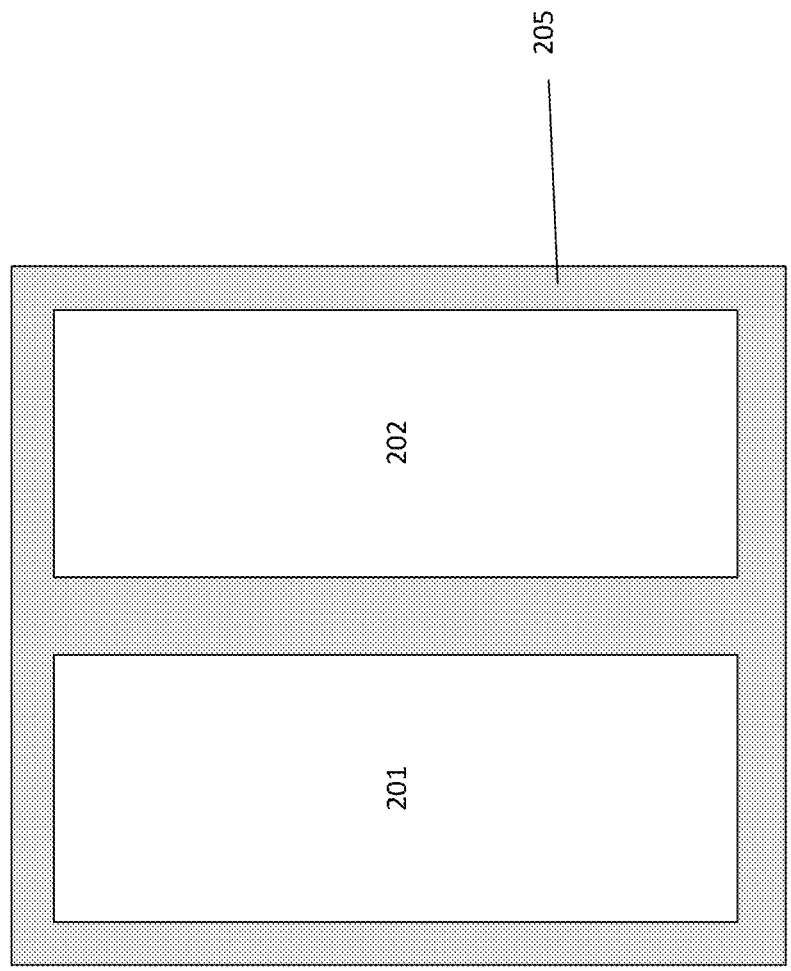

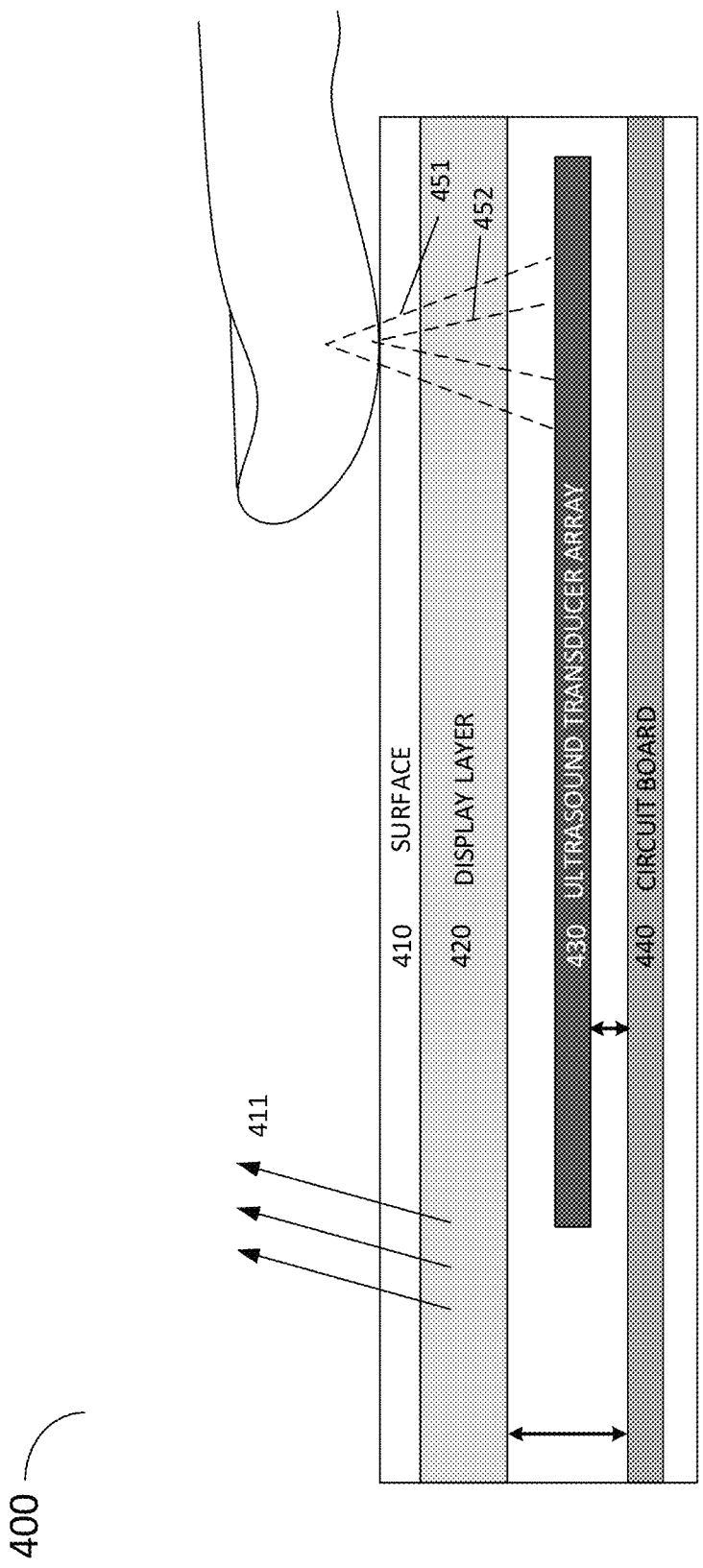

US 11,354,926 B2

ULTRASOUND FINGERPRINT DETECTION AND RELATED APPARATUS AND METHODS

CROSS-REFERENCE TO RELATED APPLICATIONS

The present application claims the benefit under 35 U.S.C. § 119(e) of U.S. Patent Application Ser. No. 62/776,922, filed Dec. 7, 2018, and entitled "ULTRASOUND FINGERPRINT DETECTION AND RELATED APPARATUS AND METHODS," which is hereby incorporated herein by reference in its entirety.

BACKGROUND

Field

The present application relates to fingerprint detection using ultrasound.

Related Art

Some micromachined ultrasonic transducers include a flexible membrane suspended above a substrate. A cavity is located between part of the substrate and the membrane, such that the combination of the substrate, cavity, and membrane form a variable capacitor. If actuated, the membrane may generate an ultrasound signal. In response to receiving an ultrasound signal, the membrane may vibrate, resulting in output of an electrical signal.

BRIEF SUMMARY

Ultrasound fingerprint detection apparatus and methods are described. In some aspects, the fingerprint sensor includes an ultrasound-on-a-chip device having microfabricated ultrasonic transducers integrated with circuitry. The circuitry may be integrated circuitry of a complementary metal oxide semiconductor (CMOS) substrate. The fingerprint sensor may be part of a smartphone, tablet computer, laptop computer, or other device for which detecting a fingerprint is desired.

According to some aspects, an ultrasound fingerprint apparatus is provided comprising a micromachined ultrasonic transducer comprising a substrate having a cavity, a membrane coupled to the substrate such that the cavity separates the membrane from at least a portion of the substrate, and first and second electrodes on the substrate and opposite the membrane arranged so that at least part of the first electrode is arranged within the interior of at least a portion of the second electrode.

According to some aspects, an ultrasound fingerprint apparatus is provided comprising a micromachined ultrasonic transducer configured to emit ultrasound of at least two different frequencies and to detect a fingerprint based on detection of the emitted ultrasound of the at least two different frequencies.

According to some aspects, a mobile electronic device with fingerprint detection is provided comprising a housing, an ultrasound-on-a-chip device disposed within the housing, and a display coupled to the housing, wherein the ultrasound-on-a-chip device is disposed between the housing and the display and configured to emit through the display ultrasound of a first frequency spectrum and ultrasound of a second frequency spectrum, different from the first frequency spectrum.

According to some aspects, a method of detecting a fingerprint is provided, the method comprising emitting, from a micromachined ultrasonic transducer, ultrasound of a first frequency spectrum and receiving first ultrasound reflected from a finger, emitting, from the micromachined ultrasonic transducer, ultrasound of a second frequency spectrum, different from the first frequency spectrum, and receiving second ultrasound reflected from the finger, and detecting the fingerprint based at least in part on the received first ultrasound and the received second ultrasound.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIG. 1 depicts an ultrasound fingerprint sensor detecting a subject's finger at multiple depths, according to a non-limiting embodiment;

FIGS. 2A-2D depict dual-electrode capacitive micromachined ultrasonic transducers, according to non-limiting embodiments;

FIGS. 4A-4B depict exterior and cross-sectional views, respectively, of a mobile telephone comprising an ultrasound fingerprint sensor, according to a non-limiting embodiment;

DETAILED DESCRIPTION

Figure 2A:
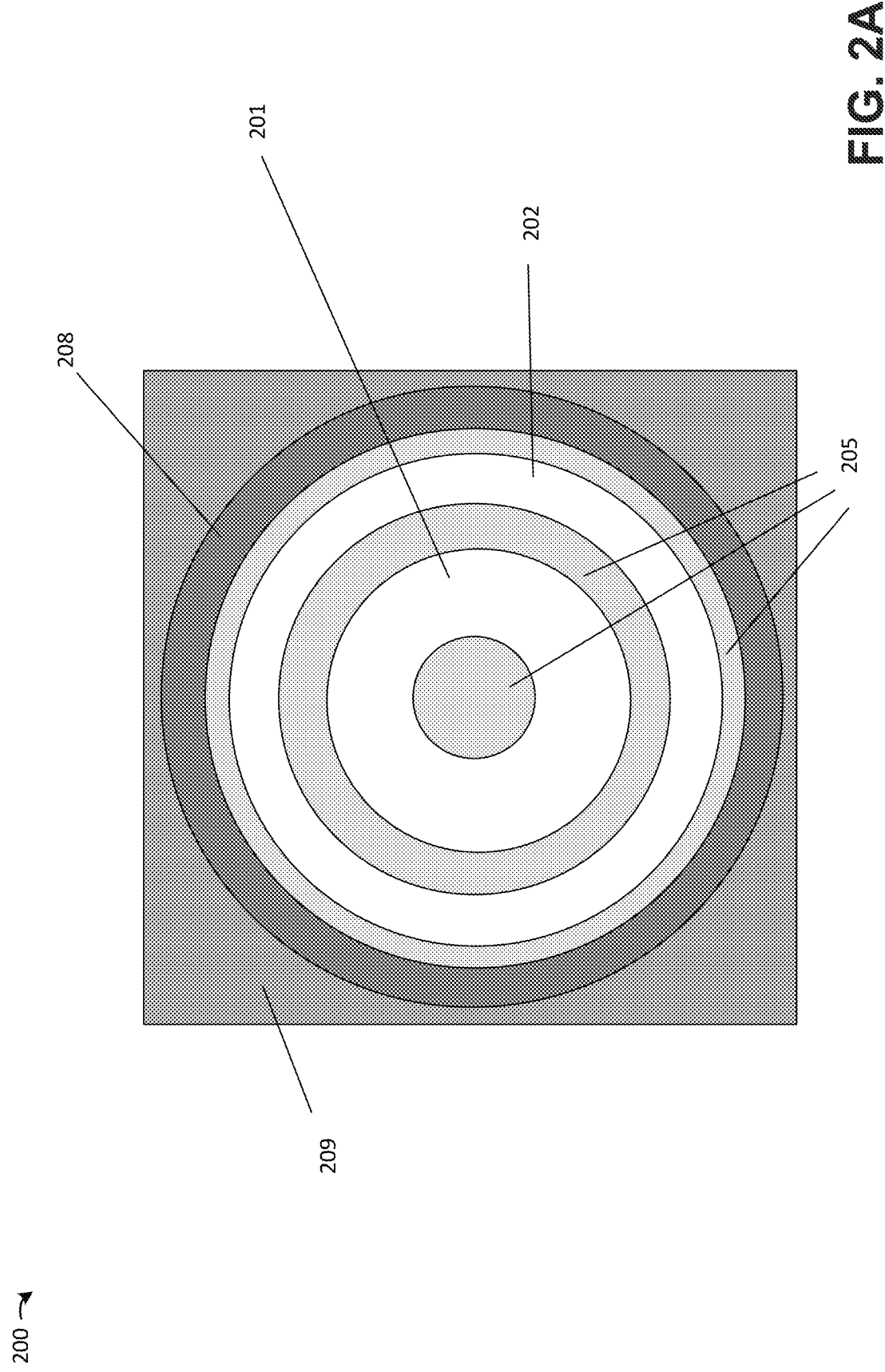

Aspects of the present application provide techniques for ultrasound fingerprint detection. In some embodiments, an ultrasound fingerprint sensor may operate at multiple different frequencies to image different aspects—such as different depths for example—of a subject's finger. As referred to herein, the operation of an ultrasound sensor at different frequencies refers to production of ultrasound with two different frequency spectra, which may include, but is not limited to, ultrasound with a first peak frequency and ultrasound with a second peak frequency different than the first peak frequency. The techniques described herein resolve different depths of a fingerprint being scanned via the application of two or more different ultrasound signals. According to some embodiments, these techniques may be applied in cases where the two or more signals probe different depths in the finger through some difference in their respective frequency spectra, wherein a wide variety of such differences may be envisioned.

Since different ultrasound frequencies are expected to penetrate a subject's finger to different depths degrees, probing or imaging a finger using multiple ultrasound peak frequencies or frequency bands may provide information on different physical aspects of the finger. For instance, some ultrasound frequencies may reflect from the surface of the skin, and then be used to sense a surface of the skin, whereas other ultrasound frequencies may penetrate through one or more of the epidermal, dermal and/or subcutaneous layers and therefore be used to sense features beneath the surface of the skin. In some embodiments, the ultrasound fingerprint sensor employs a dual-electrode configuration to generate and detect different peak ultrasound frequencies. The "dual-electrode" nature of this configuration refers to one side of the capacitive transducer cavity; it will be appreciated that an ultrasound fingerprint detector may include one or more electrodes opposing the "dual-electrode" side of the transducer. The ultrasound fingerprint sensor may have utility in various applications, including but not limited to mobile electronic devices, such as mobile phones or tablet computers, a laptop computer or biometric access equipment (e.g., a fingerprint sensor terminal).

While embodiments described herein are arranged with the "dual-electrode" side of the transducer being below the cavity, it will be appreciated that the dual-electrode side of the transducer could instead be arranged above the cavity. There may be an advantage to arrange the dual-electrode side below the cavity to be closer to other electronic components to which it is coupled, but in principle either arrangement may be employed.

Aspects of the present application provide an ultrasound fingerprint sensor configured to produce ultrasound signals of at least two different frequencies and to sense reflections of the ultrasound signals from a subject's finger. It will be appreciated that references herein to detection of a "fingerprint" may refer to detection of any physiological features of a user relating to the fingertip, and may not directly relate to the ridges of the epidermal fingerprint. For instance, measurements of subcutaneous features of a user's finger may be representative of that user, and may in some cases be unique, though measurements of these features may not directly measure epidermal ridges. Measurements of these types are considered herein to all relate to the "fingerprint" of a user as determined via the techniques described.

FIG. 1 depicts an example of an ultrasound beam extending from an ultrasound fingerprint sensor to two different depths, D1 and D2, of a subject's finger, according to some embodiments. The ultrasound fingerprint sensor may in some cases comprise a capacitive micromachined ultrasonic transducer (CMUT), and in some cases may comprise an array of CMUTs which together perform sensing of a target. In the example of FIG. 1, a subject's finger 105 may be scanned at two different depths D1 and D2 by ultrasound signals 111 and 112 of different frequencies. In the example of FIG. 1, the depth D1 is at the surface of the skin of finger 105 and depth D2 is below the surface of the skin. For purposes of clarity a small gap is shown in the figure between the finger 105 and the sensor 110, although it will be appreciated that in some cases such a gap may not be present, and in fact it may be desirable for there to be no gap between the finger and sensor to reduce reflections of the ultrasound signal as it travels from the ultrasound fingerprint sensor to the finger 105. The ultrasound signals 111 and 112 are emitted by an ultrasound fingerprint sensor 110, simultaneously or sequentially. In some embodiments, the ultrasound fingerprint sensor 110 may be, or may be part of, an ultrasound-on-a-chip device. According to some embodiments, the depths D1 and D2 may each be less than one-half of an inch. For instance, a distance from an upper surface of a CMUT (or array of CMUTs) to a focus point of either or both of the beams 111 and 112 may be less than one-half of an inch.

In some embodiments, to produce different ultrasound frequencies, a CMUT may be operated at different bias voltages to produce different resonant frequencies. As a non-limiting example, a CMUT may be operated in two frequency bands to provide for two separate modes of imaging by sensing different depths as discussed above. The CMUT may be operated at a DC bias voltage of 95% of its collapse voltage for low frequency (2-5 MHz) imaging beneath the epidermis; and at a DC bias voltage above collapse voltage for high frequency (12-17 MHz) imaging of the fingertip. The listed DC bias voltage operating points are non-limiting, as other bias voltages may be applied to achieve different operating frequencies.

Aspects of the present application provide an ultrasound fingerprint sensor that includes at least two electrodes configured to receive electrical signals of different frequencies resulting in generation of ultrasound signals of different frequencies, for example through control of a membrane of a capacitive ultrasonic transducer. A multi-electrode scheme may provide for improved transmission and reception efficiency both in and out of collapse for multiple frequency ranges. As a non-limiting example, FIG. 2A depicts a top view of a dual-ring electrode design of a capacitive micro-machined ultrasonic transducer configured to sense a subject's skin using two different frequencies. FIG. 2A depicts an electrode configuration opposite the membrane of a CMUT of an illustrative ultrasound fingerprint sensor 200. The illustrated electrodes may represent bottom electrodes of a capacitive micromachined ultrasonic transducer. The sensor 200 may comprise one or more additional electrodes on the membrane itself, but those are not shown in this figure. Sensor 200 includes electrodes 201 and 202, which are concentrically aligned electrodes configured to produce ultrasound of different frequencies through suitable control of a membrane of the transducer. For instance, electrode 201 may be configured to produce comparatively lower frequency ultrasound (e.g., between 1 MHz and 10 MHz), whereas electrode 202 may be configured to produce comparatively higher frequency ultrasound (e.g., between 10 MHz and 40 MHz). Regions 205 and 209 comprise dielectrics (e.g., oxides) and region 208 comprises a by-pass bonding area for bonding a lower substrate comprising the illustrated electrodes with a membrane, in the non-limiting example of FIG. 2A.

Figure 2B:
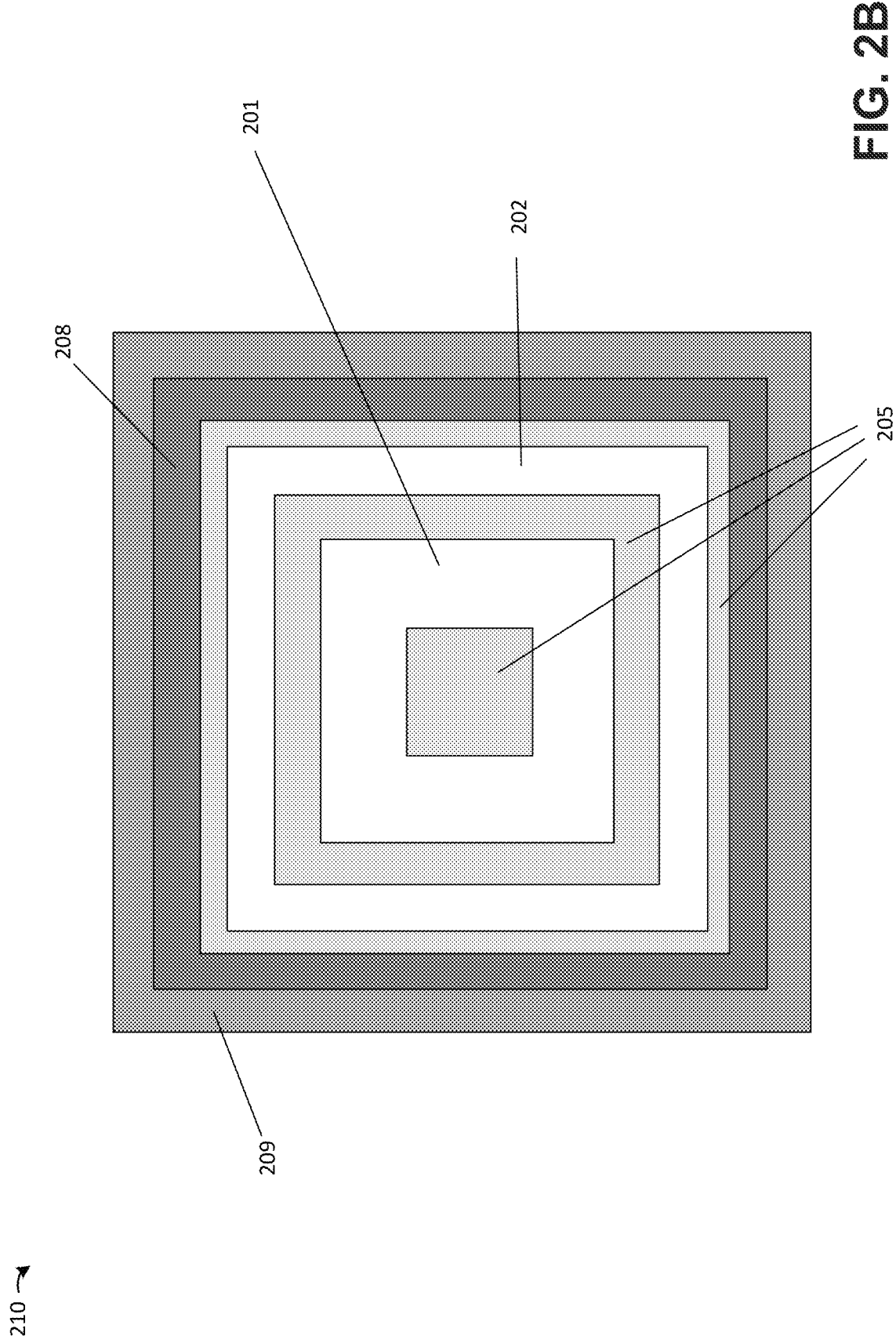
Figure 2C:
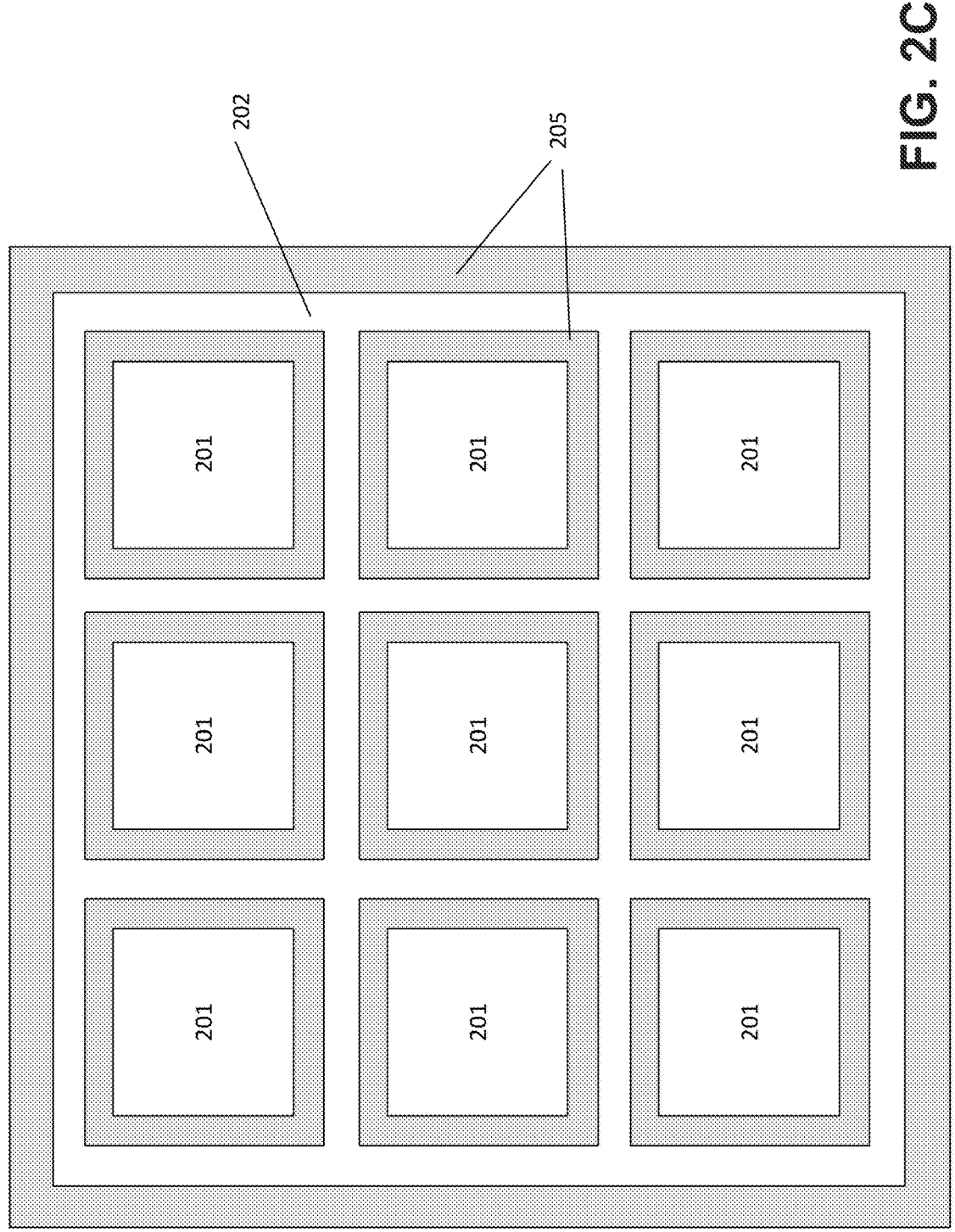

As further non-limiting examples, FIGS. 2B-2D depict additional multi-electrode designs 210, 220 and 230, with elements provided the same labels as in the example configuration of FIG. 2A. These examples illustrate further shapes of suitable multi-electrode designs, including concentric squares in FIG. 2B, a grid electrode containing secondary electrodes in the grid spaces in FIG. 2C, and side-by-side rectangular electrodes in FIG. 2D. Other shapes of electrodes may alternatively be implemented, as the various aspects of the application relating to a multi-electrode structure for generating multiple ultrasound frequencies are not limited to the particular shapes of the electrodes.

Figure 2E:
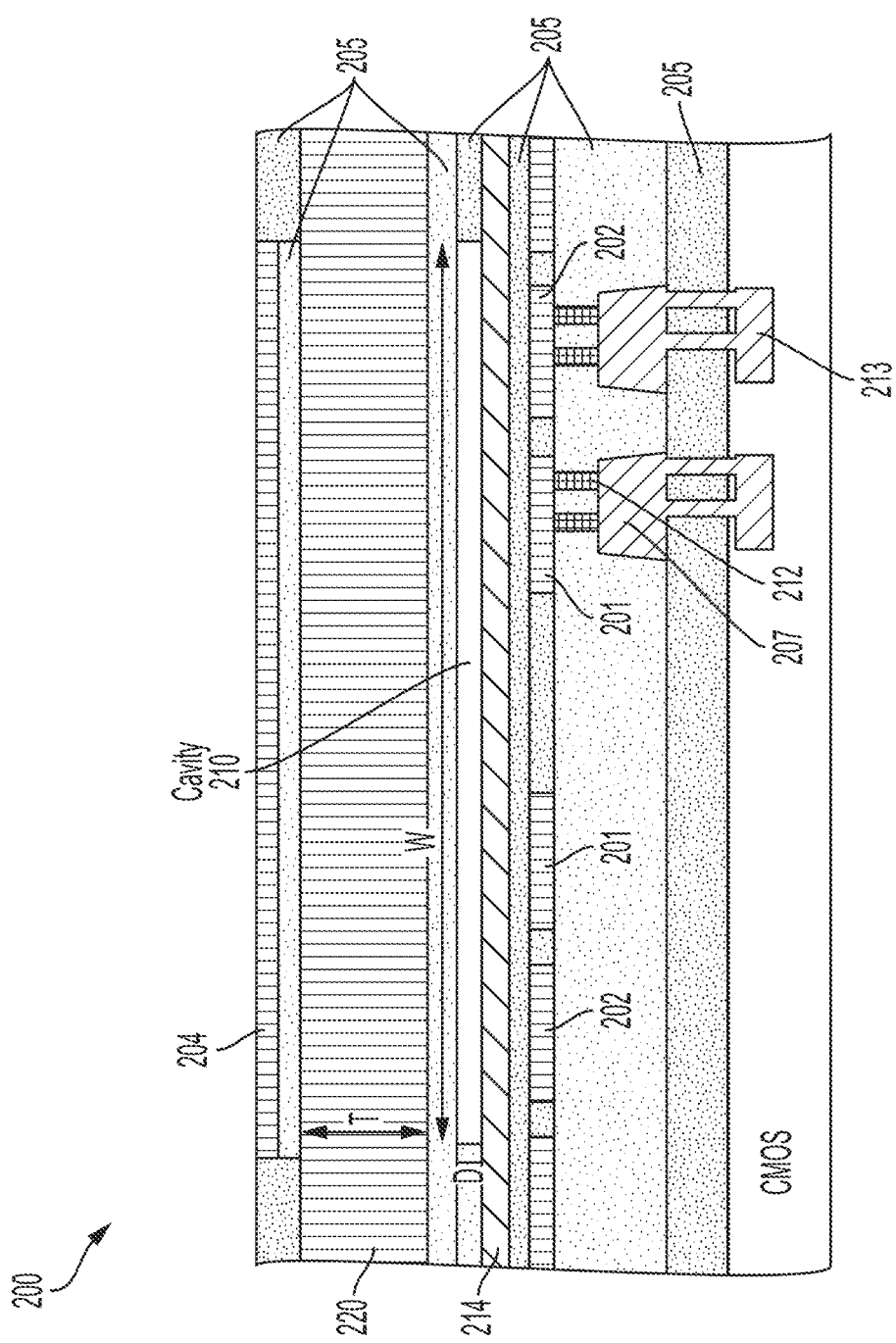
FIG. 2E depicts a cross-sectional view of the dual-electrode capacitive micromachined ultrasonic transducer of FIG. 2A, according to a non-limiting embodiment.

FIG. 2E depicts a non-limiting example of a cross-sectional view of the illustrative dual-ring electrode design of FIG. 2A, and incldues a cavity 210 of width W and depth D in addition to a silicon membrane 220 of thickness T. Electrodes 201 and 202 are shown in cross section and, since they have a ring shape, appear as two distinct regions in the cross-section shown in FIG. 2E. The electrodes 201 and 202 (e.g., Ti electrodes) are each coupled to respective driving components 207 (e.g., AlCu) and 213 (e.g., Cu) through vias 212 (e.g., tungsten vias). A cavity 210 is arranged above the electrodes 201 and 202, with a layer of atomic-layer-deposited (ALD) alumina 214 being arranged between the electrodes and the cavity. A silicon membrane 220 is arranged above the cavity and, in some embodiments, may be configured to operate as a secondary electrode to electrodes 201 and 202. That is, the silicon membrane 220 may represent an opposite electrode to the capacitive transducer, opposite to electrodes 201 and 202. A MEMS passivation layer 204 (e.g., SiO/SiN) is deposited over the silicon membrane 220. Oxide layers 205 are arranged between the above-described layers as shown in FIG. 2E. During operation, a DC bias voltage may be applied to the conductive silicon membrane 220.

It should be appreciated that, although the examples of FIGS. 2A-2D depict multiple electrodes arranged within the same plane of a fingerprint sensor, in some cases lower electrodes of a fingerprint sensor may be arranged in different planes. That is, the electrodes may be arranged in at least three planes, with the upper electrode being arranged in one plane and the lower electrodes being arranged in at least two different planes. For instance, an ultrasound fingerprint sensor may comprise a first lower electrode configured to receive a first frequency electrical signal resulting in generation of comparatively lower frequency ultrasound, and a second lower electrode arranged beneath the first electrode may be configured receive a second frequency electrical signal resulting in generation of comparatively higher frequency ultrasound. Ultrasound produced by the second electrode may pass through the first electrode when transmitted from the second electrode to the finger and/or when reflected from the finger, and ultrasound produce by both the first and second electrodes may pass through an upper electrode of the device.

A non-limiting example of operating parameters for generating ultrasound signals of different frequencies is now provided. For a CMUT having a collapse voltage of approximately 52 V, an ultrasound signal of a first frequency may be generated having a 600 kPa peak-to-peak average transmit pressure over the CMUT surface for a 2 cycle, 3 MHz, 50V peak-to-peak drive pulse using a 50 V DC bias. An ultrasound signal of a second frequency may be generated by applying a 60 V DC bias, thus operating in the collapse regime, with the resonance frequency of the membrane now approximately 15 MHz. A 1 MPa peak-to-peak average pressure at the CMUT surface may be achieved with a 30V peak-to-peak drive pulse under such circumstances. A capacitive ultrasonic transducer with a dual-electrode design of the types described above may allow for achieving the operating scenarios just described, by using one electrode for the application of one of the drive pulses (e.g., the 50 V peak-to-peak drive pulse) and the other electrode for application of the other drive pulse (e.g., the 30 V peak-to-peak drive pulse). Other examples are possible.

Figure 3:
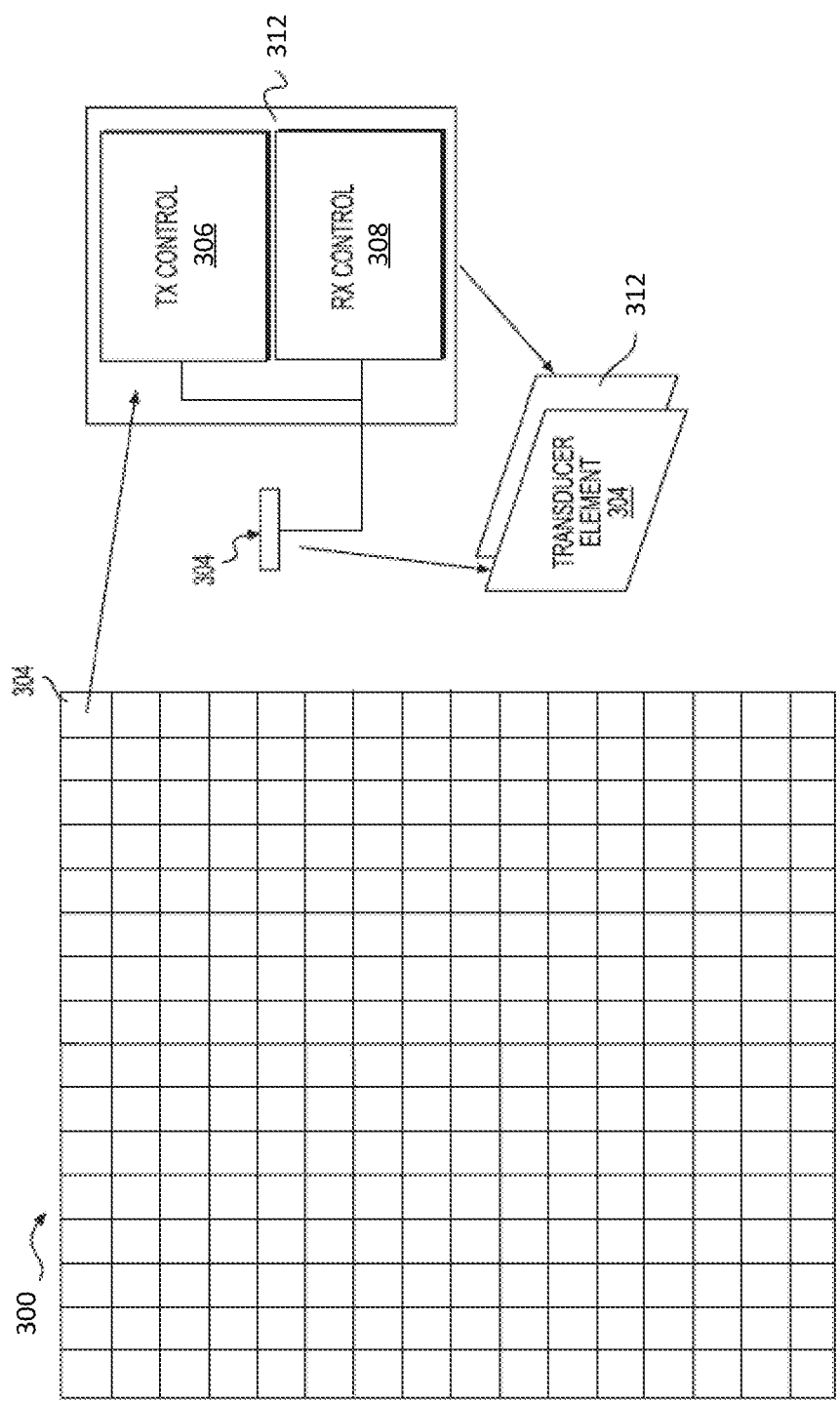
FIG. 3 shows an illustrative example of how an individual transducer element in a transducer array may be arranged with respect to CMOS circuitry for that element.

According to some aspects of the present application, an ultrasound fingerprint sensor may comprise an array of transducers, including but not limited to any number and combination of the transducers shown in FIGS. 2A-2D. FIG. 3 depicts an example of such an array, according to some embodiments.

FIG. 3 shows an illustrative example of how an individual transducer element 304 in a transducer array 300 may be arranged with respect to complementary metal oxide semiconductor (CMOS) circuitry 312 (including a transmit (TX) control circuit 306 and/or an receive (RX) control circuit 308) for that transducer element 304. As shown, in some embodiments, each transducer element 304 may have associated with it a corresponding TX control circuit 306 and a corresponding RX control circuit 308. In the embodiment shown in FIG. 3, each of the transducer elements 304 is disposed directly above its corresponding TX control circuit 306 and/or RX control circuit 308 so as to, for example, facilitate interconnections, minimize cross-talk between components, minimize parasitic capacitances, and save on semiconductor chip space, among other possible benefits. Details as to how transducer cells (e.g., transducer cells 200 or 210 described above), transducer elements 304, and transducer array(s) 300 may be integrated with or otherwise formed above CMOS circuitry in this manner are provided in U.S. patent application Ser. No. 14/208,351, entitled COMPLEMENTARY METAL OXIDE SEMICONDUCTOR (CMOS) ULTRASONIC TRANSDUCERS AND METHODS FOR FORMING THE SAME, filed on Mar. 13, 2014 and now issued as U.S. Pat. No. 9,242,275, which is hereby incorporated by reference in its entirety. Other examples may be found in U.S. patent application Ser. No. 14/635,197, entitled "MICROFABRICATED ULTRASONIC TRANSDUCERS AND RELATED APPARATUS AND METHODS," filed Mar. 2, 2015 and now issued as U.S. Pat. No. 9,067,779, which is hereby incorporated by reference in its entirety.

It should be appreciated, however, that in other embodiments one or more of the transducer elements 304 may be otherwise arranged with respect to one or more TX control circuits 306 and/or one or more RX control circuits 308, so as to achieve other benefits or advantages. In certain implementations, for example, the functionality of the TX control circuit 306 and/or the RX control circuit 308 may be performed by circuitry located on a different chip or even a different device than that on which the ultrasonic transducers are formed.

According to some aspects of the present application, an ultrasound fingerprint sensor may include at least one micromachined ultrasonic transducer with any suitable electrode dimensions, membrane thickness, cavity depth and width, and DC and AC operating points. Non-limiting examples are now provided.

In some embodiments, the in-plane diameter of an electrode structure such as those illustrative structures shown in FIGS. 2A-2E is greater than or equal to 10 μm, 15 μm, 20 μm, 25 μm or 30 μm. In some embodiments, the diameter is less than or equal to 150 μm, 100 μm, 75 μm, or 50 μm. Any suitable combinations of the above-referenced ranges are also possible (e.g., diameter of greater or equal to 25 μm and less than or equal to 100 μm, etc.).

In some embodiments, the thickness T of a silicon membrane such as membrane 220 shown in FIG. 2E is greater than or equal to 1 μm, 2 μm, 3 μm, 4 μm or 5 μm. In some embodiments, the thickness is less than or equal to 50 μm, 10 μm, 8 μm, 5 μm, or 3 μm. Any suitable combinations of the above-referenced ranges are also possible (e.g., a membrane thickness of greater or equal to 1 μm and less than or equal to 5 μm, etc.).

In some embodiments, an ultrasound fingerprint sensor may be configured to supply a DC bias voltage to the silicon membrane (e.g., membrane 220 shown in FIG. 2E) of greater than or equal to 5V, 10V, 15V or 20V. In some embodiments, the DC bias voltage is less than or equal to 100V, 75V, 50V or 25V. Any suitable combinations of the above-referenced ranges are also possible (e.g., a DC bias voltage of greater or equal to 10V and less than or equal to 50V, etc.).

In some embodiments, an ultrasound fingerprint sensor may be configured to supply an AC voltage to electrodes of the sensor (e.g., electrodes 201 and/or 202 shown in FIGS. 2A-2E) with a magnitude of greater than or equal to 5V, 10V, 15V or 20V. In some embodiments, the magnitude of the AC voltage is less than or equal to 50V, 25V, 10V or 5V. Any suitable combinations of the above-referenced ranges are also possible (e.g., an AC voltage applied to an electrode with a magnitude of greater or equal to 5V and less than or equal to 25V, etc.). It will be appreciated that an AC voltage applied to electrodes of the sensor may be of a positive or negative voltage.

In some embodiments, an ultrasound fingerprint sensor may be configured to produce ultrasound with a frequency of greater than or equal to 1 MHz, 5 MHz, 10 MHz, 20 MHz or 30 MHz. In some embodiments, the ultrasound fingerprint sensor may be configured to produce ultrasound with a frequency of less than or equal to 50 MHz, 40 MHz, 30 MHz, 20 MHz, 15 MHz or 10 MHz. Any suitable combinations of the above-referenced ranges are also possible (e.g., a frequency of greater or equal to 5 MHz and less than or equal to 15 MHz, etc.).

Cavities of the ultrasound fingerprint sensor (e.g., cavity 210) may have a depth D designed for desired operation of the ultrasonic transducers ultimately formed, for example in terms of frequency of operation. In some embodiments, the depth D may be approximately 2 microns, approximately 0.5 microns, approximately 0.25 microns, between approximately 0.05 microns and approximately 10 microns, between approximately 0.1 microns and approximately 5 microns, between approximately 0.5 microns and approximately 1.5 microns, any depth or range of depths in between, or any other suitable depth.

A cavity 210 may have a width W, also illustrated in FIG. 2E. In some embodiments, a cavity 210 may have a widths W of approximately 50 microns, between approximately 5 microns and approximately 500 microns, between approximately 20 microns and approximately 100 microns, any width or range of widths in between, or any other suitable widths.

In some embodiments, a cavity has a width W of approximately 50 microns and a depth D of approximately 0.2 microns. In some embodiments, a ratio of the width W to the depth D may be greater than 50, greater than 100, greater than 150, between 30 and 300, or any other suitable ratio. The ratio may be selected to provide desired operation of the transducer membrane, for example operation at a target frequency.

As a non-limiting example, an ultrasound fingerprint sensor may comprise dual-ring electrode structures with respective diameters of 25 μm and 100 μm, a membrane of thickness 10 μm arranged above the electrode structures, may be configured to supply a 25V DC bias voltage to the membrane and a 15V AC voltage to the electrode structures, may produce ultrasound of 5 MHz and 15 MHz from the two electrode structures, and include a cavity with a depth of 1 μm and a width of 50 μm.

Figure 4A:
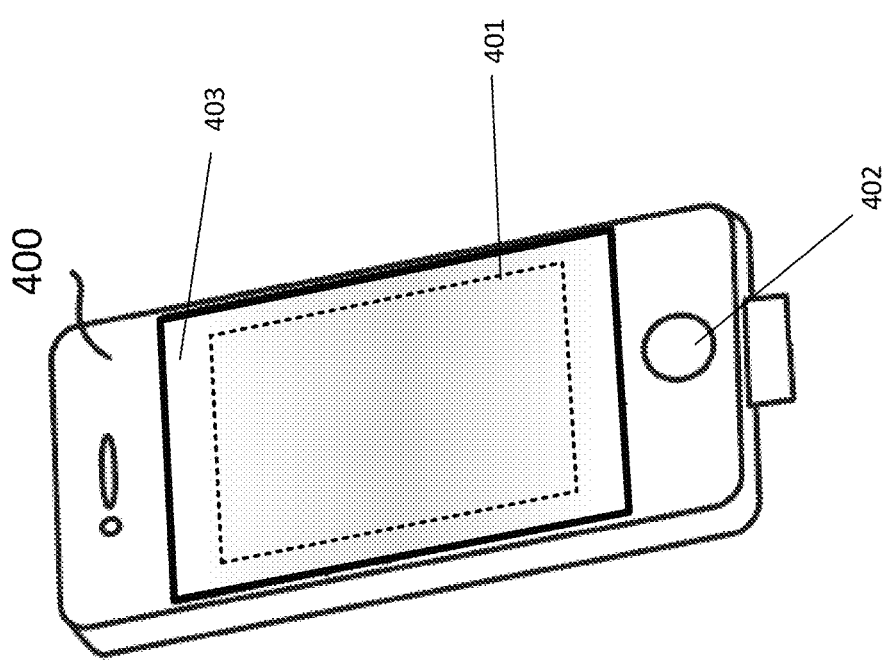

An ultrasound fingerprint sensor as described herein may be disposed in various devices including but not limited to mobile electronic devices, such as mobile phones, or biometric access equipment. FIG. 4A depicts an example of a mobile telephone 400 comprising an ultrasound fingerprint sensor 401, according to some embodiments. The sensor 401 is depicted with dashed lines to indicate that the sensor is arranged beneath the exterior surface of the telephone 400 and is not visible through said surface. While the sensor 401 is depicted in FIG. 4A as being arranged beneath a particular region of screen 403 of mobile telephone 400, it will be appreciated that the sensor 401 may be arranged beneath the screen in any suitable position and with any suitable size, and in some cases may be included beneath some or part of the button 402 of the telephone in addition to or alternatively from the screen 403. In some embodiments, the sensor 401 may be arranged under the back face of the mobile telephone 400.

FIG. 4B depicts a cross-sectional view of the mobile telephone of FIG. 4A. In the example of FIG. 4B, the mobile telephone 400 comprises a circuit board 440 electrically coupled to, and configured to control, a display layer 420 and an ultrasound transducer array 430. The display layer is configured to produce light through a surface 410 which may for instance comprise glass or transparent plastic, and may for instance comprise an LED display or an OLED display. The ultrasound transducer array 430 is configured to sense a subject's finger by emitting ultrasound of multiple frequencies 451 and 452, to thereby sense different depths of the finger, as described above in connection with FIG. 1. Ultrasound transducer array 430 may comprise any number of CMUTs arranged in a layer, such as an array comprising a number of instances of the CMUT shown in FIG. 2E.

Figure 5A:
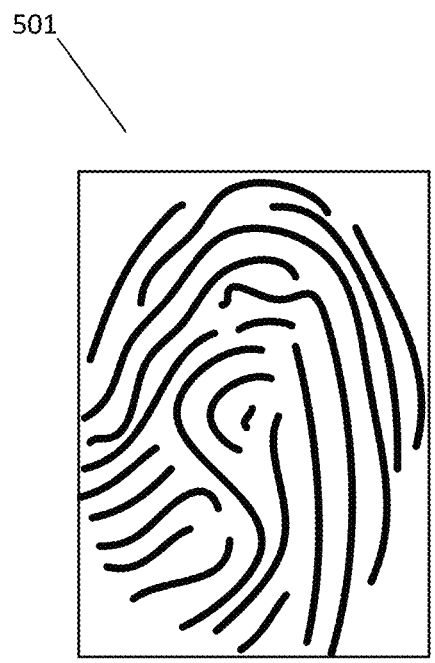
FIGS. 5A-5B depict images of a finger obtained by scanning the finger at two different depths, according to some embodiments.
Figure 5B:
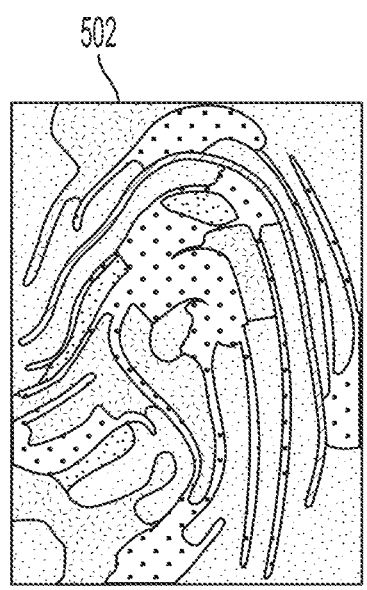

As described previously, aspects of the present application provide an ultrasound fingerprint sensor configured to image a subject's fingerprint using two different ultrasound frequencies. FIGS. 5A-5B depict illustrative images of the same finger scanned at two different depths, according to some embodiments. As discussed above, ultrasound of different frequencies produced by a CMUT may penetrate a finger to different degrees. FIG. 5A is an example of an image 510 of a finger that may be produced by scanning the finger with a comparatively high frequency (e.g., between 10 MHz and 40 MHz) to resolve surface features of the finger (e.g., the illustrated ridges of a fingerprint). FIG. 5B is an example of an image 520 of the same finger as shown in FIG. 5A that may be produced by scanning the finger with a comparatively low frequency (e.g., between 1 MHz and 10 MHz) to resolve features within the dermal and/or subcutaneous layers of the finger.

Figure 6:
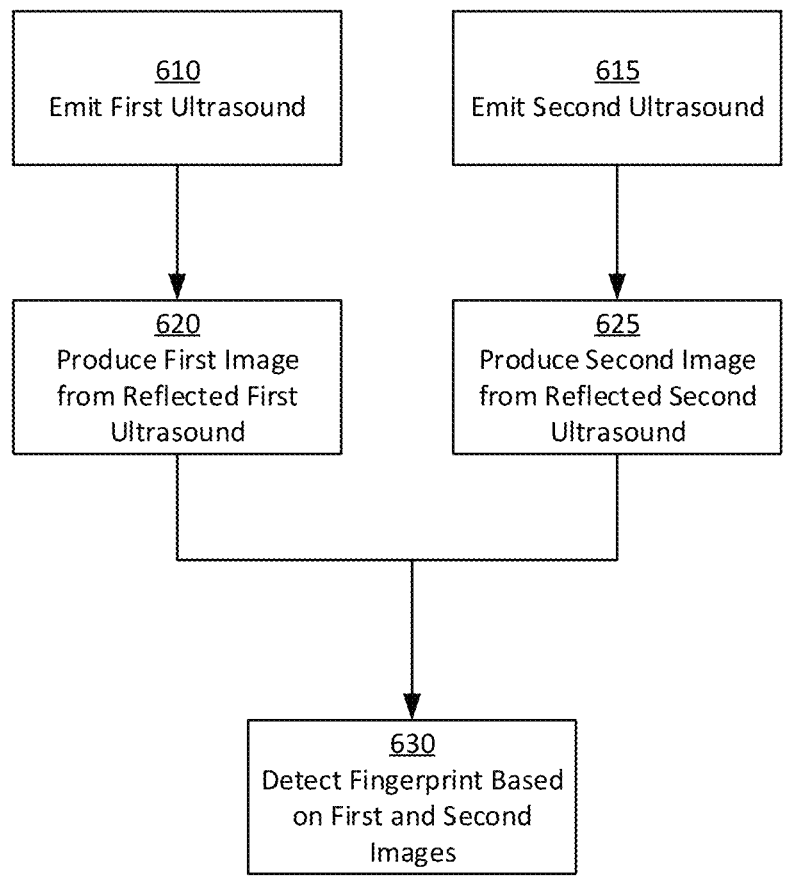
FIG. 6 is a flowchart of a method of detecting a fingerprint based on images of a finger scanned at two different depths, according to some embodiments.

FIG. 6 is a flowchart of a method of detecting a fingerprint, according to some embodiments. In method 600, first and second ultrasound signals are emitted in acts 610 and 615, which may be performed sequentially, or at least partially at the same time. The first and second ultrasound signals emitted in acts 610 and 615 are both incident upon a finger of a user, as discussed further above. The first and second ultrasound signals may exhibit different frequency spectra such that different depths of the finger are probed by the two ultrasound signals. As discussed above, in some cases the use of different frequency spectra may mean that the peak frequency of each spectrum is different, although other differences may be exhibited between the frequency spectra in addition, or as an alternative to the different peak frequencies.

In acts 620 and 625, reflected signals produced through emission of the first and second ultrasound signals in acts 610 and 615 are received and images of the finger generated according to the received signals. It will be appreciated that acts 620 and/or 625 may be performed during the same time as at least part of acts 610 and/or 615. For instance, the first image of the finger may be produced whilst the first ultrasound continues to be emitted and/or whilst the second ultrasound is being emitted. Irrespective of the temporal ordering of acts 610, 615, 620 and 625, in act 630 a fingerprint is detected based on the produced first and second images. According to some embodiments, act 630 may comprise a comparison of the first and/or second images with previously obtained images of a finger to determine whether the finger currently being scanned matches the previously scanned finger. According to some embodiments, act 630 may comprise a comparison between the first and second images. Such a comparison may have numerous benefits such as, but not limited to, preventing an imposter from spoofing a user's fingerprints.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound fingerprint apparatus, comprising:
   one or more micromachined ultrasonic transducers, each comprising:
      a substrate having a cavity;
      a membrane coupled to the substrate such that the cavity separates the membrane from at least a portion of the substrate; and
      first and second electrodes disposed on the substrate opposite the membrane, wherein at least a portion of the first electrode is disposed within at least a portion of the second electrode; and
   integrated circuitry, disposed in the substrate, that provides a first electrical signal having a first frequency to the first electrode and a second electrical signal having a second frequency to the second electrode.

2. The ultrasound fingerprint apparatus of claim 1, wherein the first and second electrodes are ring-shaped electrodes, and the first electrode is disposed concentrically within the second electrode.

3. The ultrasound fingerprint apparatus of claim 1, wherein the first electrical signal has a higher frequency than the second electrical signal.

4. The ultrasound fingerprint apparatus of claim 3, wherein the first drive electrical signal has a frequency between 10 MHz and 40 MHz and wherein the second electrical signal has a frequency between 1 MHz and 10 MHz.

5. The ultrasound fingerprint apparatus of claim 1, wherein the integrated circuitry is disposed in the substrate beneath the cavity.

6. The ultrasound fingerprint apparatus of claim 1, wherein the ultrasound fingerprint apparatus is an ultrasound-on-a-chip apparatus.

7. The ultrasound fingerprint apparatus of claim 1, comprising an array of the micromachined ultrasonic transducers integrated with the integrated circuitry.

8. The ultrasound fingerprint apparatus of claim 7, wherein the micromachined ultrasonic transducers are capacitive micromachined ultrasonic transducers (CMUTs).

9. The ultrasound fingerprint apparatus of claim 8, wherein the array of CMUTs focuses an ultrasound beam within one-half of an inch of an upper surface of the array of CMUTs.

10. The ultrasound fingerprint apparatus of claim 1, wherein the cavity has a width of between 5 microns and 500 microns.

11. The ultrasound fingerprint apparatus of claim 1, wherein the membrane comprises silicon.

12. An ultrasound fingerprint apparatus, comprising:
   a micromachined ultrasonic transducer, comprising a substrate and first and second electrodes, that emits ultrasound of at least two different frequencies and detects a fingerprint based on detection of the emitted ultrasound; and
   integrated circuitry, disposed in the substrate, that provides a first electrical signal having a first frequency to the first electrode and a second electrical signal having a second frequency to the second electrode.

13. An OLED display comprising the ultrasound fingerprint apparatus of claim 12.

14. A mobile electronic device comprising the ultrasound fingerprint apparatus of claim claim 12.

15. A mobile electronic device with fingerprint detection, comprising:
- a housing;
- a display coupled to the housing; and
- an ultrasound-on-a-chip device, disposed between the housing and the display, that emits through the display ultrasound having a first frequency spectrum and ultrasound of a second frequency spectrum, different from the first frequency spectrum, wherein
- the ultrasound-on-a-chip device comprises:
  - a micromachined ultrasonic transducer comprising a substrate and first and second electrodes; and
  - integrated circuitry, disposed in the substrate, that provides a first electrical signal having a first frequency to the first electrode and a second electrical signal having a second frequency to the second electrode.

16. The mobile electronic device of claim 15, wherein the substrate has a cavity, and
the micromachined ultrasonic transducer further comprises a membrane coupled to the substrate such that the cavity separates the membrane from at least a portion of the substrate,
the first and second electrodes are disposed on the substrate opposite the membrane, wherein at least a portion of the first electrode is disposed within at least a portion of the second electrode,
the first electrical signal provided to the first electrode causes the transducer to produce the ultrasound of the first frequency spectrum, and
the second electrical signal provided to the second electrode causes the transducer to produce the ultrasound of the second frequency spectrum.

17. A method of detecting a fingerprint, the method comprising:
- emitting, from a micromachined ultrasonic transducer comprising a substrate and first and second electrodes, ultrasound of a first frequency spectrum and receiving first ultrasound reflected from a finger;
- emitting, from the micromachined ultrasonic transducer, ultrasound of a second frequency spectrum, different from the first frequency spectrum, and receiving second ultrasound reflected from the finger;
- detecting the fingerprint based at least in part on the received first ultrasound and the received second ultrasound; and
- providing, with integrated circuitry disposed in the substrate, a first electrical signal of a first frequency to the first electrode and a second electrical signal of a second frequency to the second electrode.

18. The method of claim 17, wherein the first frequency spectrum and the second frequency spectrum exhibit different peak frequencies.

19. The method of claim 17, wherein the ultrasound of the first frequency spectrum and the ultrasound of the second frequency spectrum probe different depths of the finger.

* * * * *